United States Patent [19]

Amerongen et al.

[11] Patent Number: 5,443,832
[45] Date of Patent: Aug. 22, 1995

[54] HYDROXYAPATITE-ANTIGEN CONJUGATES AND METHODS FOR GENERATING A POLY-IG IMMUNE RESPONSE

[75] Inventors: Helen M. Amerongen, Jamaica Plain; Marian R. Neutra, Sherborn, both of Mass.; Jean-Pierre Kraehenbuhl, Rivaz, Switzerland

[73] Assignee: Institut Swisse de Recherches Experimentales sur le Cancer, Lausanne, Switzerland

[21] Appl. No.: 510,154

[22] Filed: Apr. 16, 1990

[51] Int. Cl.⁶ .................. A61K 39/39; A61K 39/02; A61K 39/12
[52] U.S. Cl. ............... 424/278.1; 424/184.1; 424/204.1; 424/234.1
[58] Field of Search ............ 424/278.1, 184.1, 204.1, 424/234.1

[56] References Cited

U.S. PATENT DOCUMENTS

| | | | |
|---|---|---|---|
| 3,599,150 | 8/1971 | Feinberg et al. | 424/92 |
| 4,016,252 | 4/1977 | Relyveld | 424/92 |
| 4,225,581 | 9/1980 | Kreuter et al. | 424/88 |
| 4,722,840 | 2/1988 | Valenzuela et al. | 424/88 |
| 4,888,170 | 12/1989 | Curtiss, III | 424/92 |
| 4,900,549 | 2/1990 | De Vries et al. | 424/92 |
| 5,008,116 | 4/1991 | Cahn | 424/491 |

FOREIGN PATENT DOCUMENTS

| | | |
|---|---|---|
| 0175286 | 3/1986 | European Pat. Off. . |
| 3721441C1 | 12/1988 | Germany . |
| 59-101145 | 6/1984 | Japan . |
| 63-196281 | 8/1988 | Japan . |
| 2206585 | 1/1989 | United Kingdom . |

OTHER PUBLICATIONS

Rolla, G. et al, "Identification of IgA, IgG . . . " Scand. J. Dent. Res., vol. 91 No. 3, pp. 186–190 (1983).
Eder-Colli L. et al, "Specific antibodies to bovine . . . " Neurochem. Int., vol 4 No. 5 (1982), pp. 383–388.
Lindberg et al (1993) Vaccine 11(2): 168–174.
Forrest et al (1993) "Effects of Parenteral Immunization on the Intestinal Immune Response to Salmonella Typhi Ty 21a as Measured Using Peripheral Blood Lymphocytes" Ref Source?.
Physiological Reviews 72=871 Kraehenbuhl et al.

*Primary Examiner*—Kay K. A. Kim
*Attorney, Agent, or Firm*—Nixon & Vanderhye

[57] ABSTRACT

A method for generating antigen-sensitized Ig-A-producing lymphoblasts in a mammal, using an immunogen comprising an antigen or antigen mixture in association with hydroxylated calcium phosphate (hydroxy apatite) is administered to a mucosal surface of the mammal.

6 Claims, 1 Drawing Sheet

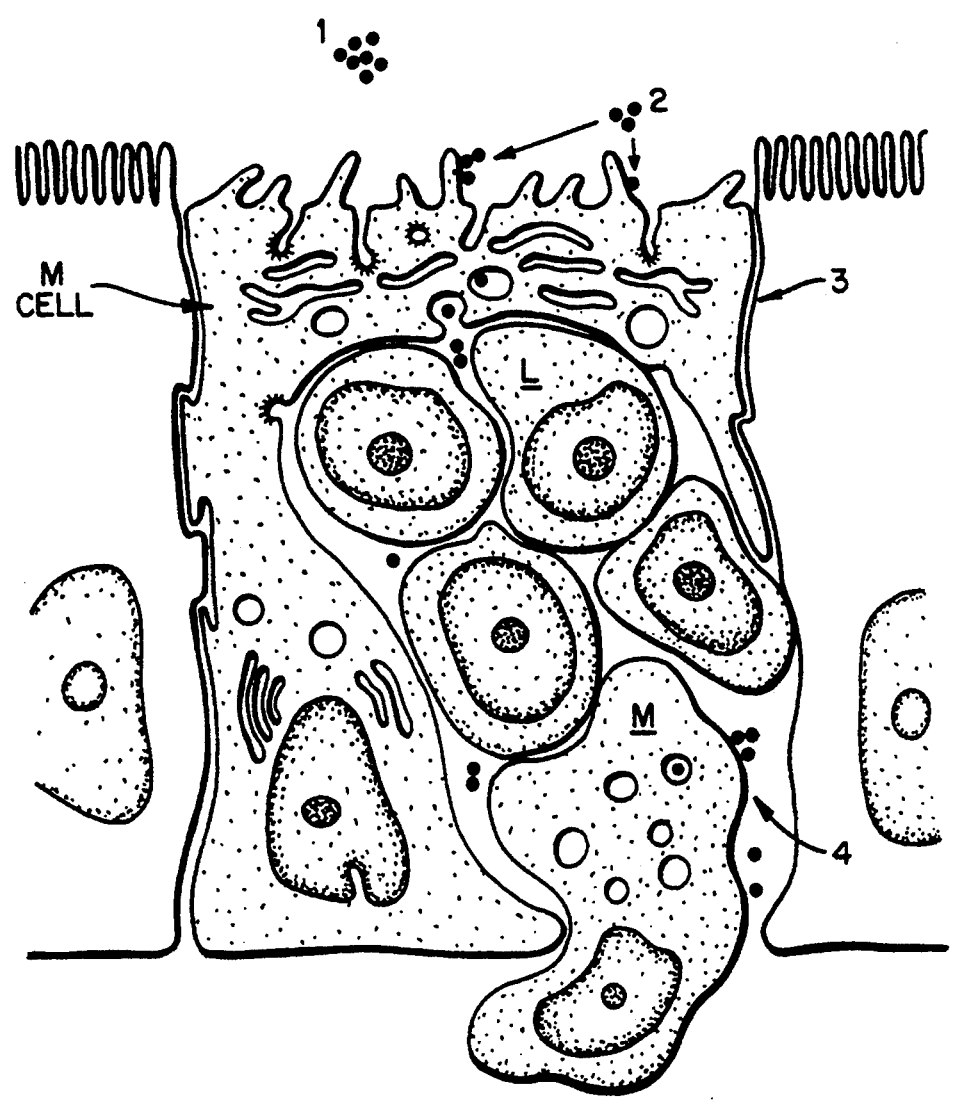

HYDROXYAPATITE-ANTIGEN CONJUGATES AND METHODS FOR GENERATING A POLY-IG IMMUNE RESPONSE

BACKGROUND OF THE INVENTION

This invention was made in part with funding from the United States Government, and the U.S. Government has certain rights in the invention.

This invention relates to the general fields of passive mucosal immune protection, and of poly-Ig immune reagents and techniques. We use the term poly-Ig to refer to the polymeric classes of antibodies-i.e. IgA and IgM. IgM antibodies are generally produced at an early stage of the immune response and are not an important factor in protective mucosal immunity. Thus, the invention generally refers to polymeric Ig antibodies, and the usual and preferred antibodies for all aspects of the invention are IgA class antibodies, which normally are secreted in dimeric form and, to a lesser degree, as higher IgA polymers.

Many pathogenic bacteria and viruses initially gain entry into the body by crossing the cellular linings (epithelia) of the gastrointestinal, respiratory, or genital tracts. A specialized class of antibodies, IgA antibodies, protects these surfaces. IgA antibodies are dimeric or polymeric molecules produced by cells located in the tissues under the epithelial surfaces. They are transported by epithelial cells into mucosal secretions, where they cross-link or coat pathogens that have not yet entered the body, preventing the pathogens from contacting and adhering to epithelial cells. Thus, IgA antibodies operate on pathogens that are outside the body, and they protect by preventing entry into the body across epithelial surfaces.

The naturally occurring IgA response is triggered by antigen delivery to mucosal surfaces. The antigen enters the body through specific sampling sites (termed microfold or M cells) that effect transepithelial antigen transport to areas of the mucosal lining containing specialized, organized collections of the cells of the mucosal immune system. More specifically, as shown in FIG. 1, antigens A (shown as filled dots) in lumen 1 bind the luminal surface of M cells at site 2. The antigens are internalized and transcytosed at 3 to be released in the intra-epithelial pocket 4 containing lymphoid cells L (B and T cells) and antigen-processing/presenting cells such as macrophage cells (M).

IgA antibodies in a naturally immunized host are transported into secretions by binding to a specific receptor (called the poly-Ig receptor) on the basal (interior) surfaces of epithelial and glandular cells throughout the respiratory and digestive systems, the genital tract, and the mammary glands. See Solari and Kraehenbuhl, "Receptor-Mediated Transepithelial Transport of Polymeric Immunoglobulins", pp. 269-298 in The Mammary Gland, Nelville and Daniel Eds., Plenum Publishing, Cambridge (1987); Mestecky (1987) J. Clin. Immunol. 7:265-276. Receptor-IgA complexes are transported across these cells and exocytosed onto luminal (exterior) cell surfaces where the receptor is enzymatically cleaved, releasing IgA into secretions along with a receptor fragment called secretory component (SC). See Mostov et. al. (1980) Proc. Nat'l Acad. Sci. U.S.A. 77:7257-7261; Solari, R. and Kraehenbuhl, J. P. Cell 36:61-71 (1984); Kuhn and Kraehenbuhl, J .Biol. Chem. 256:12490-12495(1981). It is reported that secretory component reduces proteolytic degradation of IgA. Lindh, J., J. Immunol. 114:284-286 (1975); Brown, Neucomb, Ishizaka, J. Clin. Invest. 49:1374 (1974).

In general, existing immunization strategies which involve injection of antigens evoke production of the IgG class of antibodies that circulate systemically and neutralize pathogens after they have entered the body. Injection of antigens does not generally evoke a substantial IgA response.

Efforts to take advantage of IgA protection at mucosal barriers involve oral immunization, either for active protection of the immunized mammal or for passive protection of another mammal using mucosal secretion of the immunized mammal. Glass et. al., New Eng. J. Med., 308:1389-1392 (1983); Fubara et. al., J. Immunol., 111(2):395-403 (1973). Monoclonal IgA antibodies have been produced and applied directly to respiratory mucosal surfaces in an effort to protect against pathogen entry. Mazanec et. al. J. Virol., 61:2624-2625 (1987).

Active immunization may involve challenge at the mucosal surface with intact (killed) bacteria or viruses. To avoid dangers that may be associated with this approach for certain pathogens, component antigens, such as immunogenic surface components of the pathogen, are applied at a mucosal surface. In some cases, the antigens have been conjugated to larger molecules. For example, the cholera toxin B subunit has been conjugated to antigens. See, Czerkinsky et. al. who report oral administration of a streptococcal antigen coupled to cholera toxin B subunit in Infection and Immunity 57:1072-1077 (1989). Biodegradable microspheres have also been used as an antigen carrier. For example, Eldridge et. al. Curr. Top. Microbial Immunol. 146:59 et. seq. (1989) report incorporation of antigen into biodegradable microspheres. The dry protein antigen is dispersed in a copolymer matrix without chemical conjugation.

SUMMARY OF THE INVENTION

We have discovered that hydroxylated calcium phosphate (HCP) particulate is a particularly useful carrier for antigens to be applied to mucosal surfaces. The antigen-HCP conjugate is transported across epithelium where it raises a poly Ig immune response.

One aspect of the invention generally features a method for generating antigen-sensitized Ig-A-producing lymphoblasts in a mammal. In that method, an immunogen comprising an antigen or antigen mixture in association with hydroxylated calcium phosphate (HCP) particulate is administered to a mucosal surface of the mammal. In preferred embodiments of this first aspect of the invention, the antigen-sensitized lymphoblasts are recovered and immortalized to yield an Ig-A producing hybridoma.

A second aspect of the invention features a method for vaccinating a mammal (especially a human) comprising administering the above-described immunogen to a mucosal surface of the mammal.

A third aspect of the invention features an immunogen comprising an antigen or antigen mixture in association with hydroxylated calcium phosphate particles of a size suitable for transport across epithelium.

In preferred embodiments of any of the three aspects of the invention the hydroxylated calcium phosphate is in the form of microparticles suitable for transport across the epithelium. Also preferably, the antigen comprises an externally available determinant of a pathogen or of spermatozoa, such as a viral coat or envelope protein, a lipopolysaccharide or a cell-surface protein. One form of HCP is hydroxyapatite (HA), a commercially available crystalline hydroxylated calcium phosphate discussed below.

The preferred modes of administrations of the immunogen according to the first two aspects of the invention are orally, vaginally, nasally, rectally, ocularly or to the middle ear. Oral administration can provide delivery to other G.I. mucosa including the intestinal mucosa.

The invention provides an efficient, polyvalent immunogen that can adhere to the mucosa and can be transported efficiently across the epithelial barrier for presentation to the mucosal immune system. Adsorption of proteins to HCP is relatively simple, rapid and cheap, making the invention economically feasible. Moreover, HCP has a high general affinity for the antigens of interest, including proteins and other antigens, making the invention broadly applicable. HCP is generally non-toxic, as evidenced by the fact that HA is an integral component of bone, and the systemic immune system routinely encounters HA during normal bone resorption, a process that occurs constantly at a microscopic level in healthy individuals. Accordingly, pure HA presumably can be safely administered without a host immune response, and administration can be repeated as a vehicle for the same or different antigens, without an anti-vehicle immune response. Moreover HCP, particularly HA, is relatively inexpensive. HA can readily be reduced to a size suitable for transepithelial transport by M cells; and such a reduced size is suitable for ingestion by macrophages and other cells of the reticuloendothelial system, so as to enhance immune response. Finally, M-cell uptake and transport of immunogens according to the invention is relatively selective.

Other features and advantages of the invention will be apparent from the following description of the preferred embodiments thereof.

DESCRIPTION OF THE PREFERRED EMBODIMENTS

FIGURES

FIG. 1 is a diagrammatic representation of transcytosis of antigen across M cells.

REAGENTS

In general, the methods and materials described below can be used as part of strategies for IgA protection which are disclosed in greater detail in a commonly owned patent application filed by Neutra, Kraehenbuhl, and Weltzin, simultaneously with this application, entitled SYNTHETIC POLY-Ig RECEPTOR, RECEPTOR-ANTIBODY COMPLEXES, PRODUCTION AND USE THEREOF, which application is hereby incorporated by reference. In particular, immunogens and methods according to the invention can be used with stabilizer protein as described in the above-referenced application to create poly Ig reagents for passive immunization.

The preferred embodiments of the invention feature hydroxyapatite-antigen conjugates and their use. Specifically, hydroxyapatite is a modified form of crystalline calcium phosphate, $Ca_{10}(PO_4)_6(OH)_2$. It is used as a protein fractioning reagent, due to its generalized protein-binding ability. Commercially available HA generally consists of slab-like crystals that are chemically and physically analogous to inorganic HA in normal bone tissue. As long as the starting material is free of contaminants, ingestion of HA should be relatively safe as evidenced by the existence of nutritional calcium/phosphorus supplements derived from ground bone, which are designed to be ingested.

Commercial high resolution HA (from Calbiochem) consists of crystals varying widely in size. As provided by manufacturers, HA crystals are likely to be too large, on the whole, to efficiently cross epithelial barriers. For example, crystals over 1 $\mu$m in length are unlikely to be taken up by M cells. Therefore, for use in the invention, commercial HA crystals are broken into small, relatively uniform crystalline fragments, e.g., by sonication. The resulting sonicated crystals vary somewhat in size but their size generally does not exceed 1 $\mu$m. Preferably a substantial portion of the HA is present as fragments of about 0.01–0.1$\mu$m. Fragmentation may be measured either by electron microscopy and light scattering, using standard techniques.

HA binds most proteins with high avidity and speed at low or physiologically safe concentrations. Binding is thought to depend on interaction of calcium sites with acidic and phosphate groups of proteins, and interaction of phosphates with basic protein groups. Higher molecular weight proteins will tend to be more tightly adsorbed to HA, but protein charge also plays a role. One gram of HA, for example, can bind about 30 mg of bovine serum albumin. Thus, HA can efficiently trap protein antigen from dilute solutions without addition of crosslinking chemicals, without harsh or denaturing conditions, and without wasting valuable pure antigen.

USE

HA-adsorbed antigens can be used in active vaccination of humans or other mammals. The invention is particularly useful to protect against Pseudomonas aeruqinosa, Hemophilus influenzae, Vibrio cholerae, Bordetella pertussis, Corynebacterium diphtheriae, Escherichia coli, Salmonella and typhimurium, Clostridium perfringens and other enteric clostridiae, Shigella dysenteriae, Shiqella flexnerii Neisseria gonorrheae, Trichomonas, Entameba histolytica, Giardia lamblia, Streptococcus, respiratory syncytial virus, rotavirus, reovirus, Human Immunodeficiency Virus, Human T-Cell Lymphotrophic Virus, Types I and II, polio virus, Rhinovirus, influenza virus, herpes viruses, human papilloma virus; AIDS 2° pathogens such as Pneumocystis, and yeast such as monilia. The invention is also useful to protect against allergens that contact the respiratory or digestive mucosal surfaces. It is also useful to protect against pregnancy by cross-linking spermatozoa in the vagina, and preventing their movement through the cervix and uterus.

In each case, an appropriate known antigen-e.g. whole pathogen or specific externally presented antigens such as the vital coat protein, or bacterial cell-surface proteins, pilus protein, lipopolysaccharides, viral capsid or envelope protein, protozoal plasma membrane surface component, spermatozoal surface proteins, or respiratory allergens-are used. Toxoids, e.g. CRM-197, and inactivated diphtheria toxin reported by Uchida et. al. J. Biol. Chem. 248:3838–3844 (1973) may be used. The antigen is used according to the above procedure to generate hybridomas secreting the desired protective antibodies. As just a few examples, WO88/08437 (hereby incorporated by reference) discloses atcPA pilus protein suitable for forming anti-V. cholerae monoclonal poly-Ig antibodies. U.S. Pat. No. 4,725,669 discloses the HIV (HTLV-III) envelope glycoprotein suitable for forming anti-HIV poly-Ig monoclonal antibodies. The following patents and patent applications disclose preparation of antigens for protection against Streptococcal infections, particularly infection by Group B Streptococcus: U.S. Pat. No. 4,367,221; 4,367,222; 4,367,223; 4,356,263; 4,207,414 (RE 31,672); and WO 87/06267.

Other suitable antigens are disclosed in Bacterial Vaccines and Local Immunity Proceedings of the Sclavo International Conf., Siena, Italy 17-19 November 1986. Specific reagents suitable for HIV antigens are disclosed in AIDS Research and Reference Reagent Program, National Institute of Health, June 1989. For example, gp 120 is sold by MicroGeneSys, Inc. Spermatozoa cell-surface antigens such as LDH-C4 are also known. See, e.g. Shaha et. al. and Talwar et. al. Vaccine 7:97-100 (1989); and Shaha et. al. Int. J. Androl. 11:479 (1988).

Of particular significance in the selection of antigens for practice of the invention is that mucosal protection involves cross-linking to prevent entry into the body, and this mechanism does not require that the polymeric antibody kill or "neutralize" the pathogen. In contrast, systemic (IgG) protection involves binding which, to be effective, generally must neutralize the pathogen. Thus, not every IgG antibody which binds to the pathogen is protective, as illustrated by the existence of monoclonal antibodies that specifically bind Vibrio cholerae, but do not neutralize it in the sense of preventing it from colonizing, growing and manifesting clinical symptoms in its host. The universe of antigens and determinants available to raise protective IgA antibodies is thus significantly increased.

Specifically, the HA-adsorbed antigen is prepared according to the method outlined above with appropriate modifications for production in bulk. The HA-adsorbed antigen or antigen mixture is compounded in a physiologically acceptable vehicle, and applied directly to or delivered to the mucosal surface tissue, e.g., to oral, nasal, rectal and/or vaginal surfaces. The preparation is administered in an aerosol, a suspension, a capsule and/or a suppository. Those skilled in the art will understand how to formulate such vehicles by known techniques.

USE

The invention is also particularly useful for manufacture of IgA-producing hybridomas. Such hybridomas are readily produced by challenging a mammal, e.g., by applying the above described composition to a mucosal surface, and then recovering a lymphoid cell from Peyer's patch mucosa or other mucosa which are rich in lymphold tissue and then fusing the lymphoid cell to a myeloma cell by known techniques. See, e.g., the above-referenced commonly owned, simultaneously filed, U.S. patent application No. 07/510,161.

The following examples are provided to illustrate, but not to limit the invention.

EXAMPLE 1

2 gm HA (Calbiochem) suspended in 20 ml PBS is sonicated with a probe sonicator for 30 minutes at room temperate, using the high setting (140, 80% duty cycle, of a Microson cell disrupter (Heat Systems Ultrasonics, Inc., Farmingdale, N.Y.). Average crystal size is approximately $0.01 \times 0.1$ $\mu$m after sonication, as measured by electron microscopy. Adequate sonication can be monitored by spectrophotometric absorbance. For example, absorbance (read at 650 nm) of a 2 mg/ml suspension before sonication was 0.108 O.D. units and after reduction of crystal size (as above), O.D. increased to 2.060.

EXAMPLE 2

HA crystals of this size, coated to saturation with proteins of various sizes ranging from 65 kD (albumin) to 450 kD (ferritin), when introduced into the intestinal lumen of mice and rabbits, were selectively bound and transported by M cells of Peyer's patch. This method effectively delivers proteins to cells of the mucosal immune system, in a particulate immunogenic form.

For oral immunization of a 25-gram mouse: a small amount (e.g., 30 $\mu$g) of protein in 200 $\mu$l PBS is mixed with an appropriate amount (e.g., 1 mg of HA for 30 $\mu$g protein) of presonicated and washed HA. The mixture is agitated for 1 hr. at 4° C., and HA is then pelleted by spinning for 2 min. at 10,000 rpm in a microfuge. The pellet is resuspended by vortexing or sonicating in 200 $\mu$l of water which may contain a buffer to neutralize gastric acid.

Other embodiments are within the following claims.

We claim:

1. A method for vaccinating a mammal to cause an immunogenic response comprising IgA antibodies, said method comprising the step of administering to a mucosal surface of the mammal an immunogen comprising an antigen or antigen mixture in association with particulate hydroxylated calcium phosphate of a size suitable for transport across epithelium.

2. The method of claim 1 in which said antigen comprises an externally available determinant of a pathogen or of spermatozoa.

3. The method of claim 2 in which said antigen is a viral coat protein, a viral envelope protein, a cell-surface lipopolysaccharide, or a cell-surface protein.

4. The method of claim 1 in which said immunogen is administered orally, vaginally, nasally, rectally, ocularly, or to the middle ear.

5. A method according to claim 1, wherein said hydroxylated calcium phosphate has a size not exceeding 1 micron.

6. A method according to claim 5, wherein said size is about 0.01 to 0.1 micron.

* * * * *

UNITED STATES PATENT AND TRADEMARK OFFICE
CERTIFICATE OF CORRECTION

PATENT NO. : 5,443,832
DATED : August 22, 1995
INVENTOR(S) : Amerongen et al.

It is certified that error appears in the above-identified patent and that said Letters Patent is hereby corrected as shown below:

Title page,
Item [73], insert -- and President and Fellows of Harvard College, Canbridge, Massachusetts, USA -- after "Switzerland".

Signed and Sealed this

Sixth Day of November, 2001

Attest:

*Nicholas P. Godici*

Attesting Officer

NICHOLAS P. GODICI
*Acting Director of the United States Patent and Trademark Office*